(12) United States Patent
Maurer

(10) Patent No.: US 8,835,129 B2
(45) Date of Patent: *Sep. 16, 2014

(54) DYNAMIC LIGHT SCATTERING FOR IN VITRO TESTING OF BODILY FLUIDS

(71) Applicant: Canadian Blood Services, Ottawa (CA)

(72) Inventor: Elisabeth Maurer, Vancouver (CA)

(73) Assignee: Canadian Blood Services, Ottawa (CA)

( * ) Notice: Subject to any disclaimer, the term of this patent is extended or adjusted under 35 U.S.C. 154(b) by 66 days.

This patent is subject to a terminal disclaimer.

(21) Appl. No.: 13/692,039

(22) Filed: Dec. 3, 2012

(65) Prior Publication Data
US 2013/0122538 A1 May 16, 2013

Related U.S. Application Data

(63) Continuation of application No. 13/001,654, filed as application No. PCT/CA2008/001255 on Jul. 4, 2008, now Pat. No. 8,323,922.

(51) Int. Cl.
*C12Q 1/04* (2006.01)
*C12Q 1/02* (2006.01)

(52) U.S. Cl.
USPC .............................................. 435/34; 435/29

(58) Field of Classification Search
USPC ..................................................... 435/34, 29
See application file for complete search history.

(56) References Cited

U.S. PATENT DOCUMENTS

| | | | |
|---|---|---|---|
| 4,080,264 A | 3/1978 | Cohen et al. | |
| 4,204,117 A | 5/1980 | Aberle et al. | |
| 4,781,460 A | 11/1988 | Bott | |
| 5,817,519 A | 10/1998 | Zelmanovic et al. | |
| 6,043,871 A | 3/2000 | Solen et al. | |
| 6,094,266 A | 7/2000 | Trainer | |
| 8,323,922 B2 * | 12/2012 | Maurer et al. | 435/34 |
| 2001/0024800 A1 | 9/2001 | Garcia-Rubio et al. | |
| 2002/0180972 A1 | 12/2002 | Ansari et al. | |
| 2004/0100630 A1 | 5/2004 | Yamaguchi et al. | |
| 2005/0250095 A1 | 11/2005 | Gabriel | |
| 2007/0041877 A1 | 2/2007 | Maurer et al. | |
| 2010/0136611 A1 * | 6/2010 | Maurer | 435/39 |

FOREIGN PATENT DOCUMENTS

WO WO-90/14588 A1 11/1990
WO PCT/US01/26167 A2 2/2002

OTHER PUBLICATIONS

Maurer-Spurej et al. (Portable dynamic light scattering instrument and method for the measurement of blood platelet suspensions. Phys. Med. Biol. 51 (2006) 3747-3758).*

Portable dynamic light scattering instrument and method for the measurement of blood platelet suspensions; Maurer-Spurej, Elisabeth, et al.; Physics in Medicine and Biology, 51 (Jul. 20, 2006) pp. 3747-3758.
Platelet Microparticles: a wide-angle perspective; Horstman, Lawrence L, et al.; Critical Reviews in Oncology/Hematology; 30, (1999) pp. 111-142.
Abrams, C.S., et al., Blood. 1990. 75(1), 128-138.
Cram, S.L. Methods in Cell Science. 2002, 24(1-3), 1-9.
Hoffmeister, K.M., et al. Cell. 2003.112(1), 87-97.
Rock, G. et al. Transfusion and Apheresis Science. 2006. 35, 145-149.
Fratantoni et al., J. Lab. Clin. Med., vol. 103 (4), pp. 620-631 (1984).
David et al., Coll. Surfaces B.: Biointerfaces, vol. 6 pp. 101-114 (1996).
Hubbell et al., Thromb Haemost, vol. 65, pp. 601-607, (1991).
Maurer-Spurej et al., Lab. Invest., vol. 81 (4), pp. 581-592 (2001).
Katz et al., IEEE Journal of Selected Topics in Quantum Electronics, vol. 9, No. 2, Mar./Apr. 2003.
Copending U.S. Appl. No. 12/525,467 and the references of record therein, 2010.
Spurej et al., Experientia, vol. 48, pp. 71-79 (1992).
D. Zelmanovic et al., Vet. Clin. Pathol., vol. 27 (1), pp. 2-9 (1998).
Eto et al., Cardiovascular Research, vol. 40 (1), pp. 223-229 (1998).
Tomida et al., Thromb. Res., vol. 92, pp. 221-228 (1998).
Yabusaki et al., Langmuir, vol. 18, pp. 39-45 (2002).
J. Seghatchian et al., "Transfus. Sci.", vol. 18, No. 1, pp. 27-32 (1997).
Devine, D. V., et al., "Platelet Aggregation is Not Initiated by Platelet Shape Change", Laboratory Investigation, Nov. 2001, vol. 81, pp. 1517-1525.
Maurer-Spurej, E. et al., "Activation Studies on Human Platelets Using Electrophoretic and quasi-elastic light scattering", Progress in Colloid & Polymer Science, 1990, -vol. 81: 151-155.
Devine D. V., et al., SP254, "Platelet Shape Change is Not Required for Aggregation-Initail Decrease of Light Transmission in Platelet Aggregometry Indicates Platelet Micro-Aggregation But Not Shape Change", Transfussion, 2000—vol. 40, Supplement.
Maurer-Spurej, E., SP145, "Novel Dynamic Light Sctattering Method for the Dertermination of Platelet Quality and Viability", Canadian Blood Services, Canada, Transfusion, 2004—vol. 44, Supplement.
International Preliminary Report on Patentablity / Written Opinion of the ISR for co-peniding PCT Application No. PCT/US2011/049271, 2012.

* cited by examiner

*Primary Examiner* — Karen Cochrane Carlson
*Assistant Examiner* — Natalie Moss
(74) *Attorney, Agent, or Firm* — Hancock Hughey LLP

(57) ABSTRACT

A method of diagnosing a pathological condition by detecting microparticles in a sample of bodily fluid using dynamic light scattering (DLS) is disclosed. The detection of microparticles in the bodily fluid by DLS may be used as an indicator of existing disease, to evaluate a risk of disease, as well, as to monitor the efficacy of a treatment for disease.

17 Claims, 9 Drawing Sheets

DYNAMIC LIGHT SCATTERING FOR IN VITRO TESTING OF BODILY FLUIDS

TECHNICAL FIELD

This application relates in general to dynamic light, scattering and, more particularly, to the detection of microparticles in bodily fluids using dynamic light scattering.

BACKGROUND OF THE INVENTION

Elevated or otherwise abnormal levels of microparticles in blood and other bodily fluids, such as urine for example, are known to be indicative of a variety of pathological conditions, including cardiovascular disease (DVD), diabetes, renal failure, etc.

For example, research has shown that CVD patients have high numbers of microparticles in their blood, which appear to be highly thrombogenic. Diabetes has been reported (European Heart J 2006: 27:817) to correlate with the presence of microparticles in the blood, and end-stage renal failure has also been linked to the presence of circulating microparticles in the blood (J Am Soc Nephrol 2005:16). Microparticles in the urine are often indicative of kidney failure. An abnormally high level of microparticles in the bodily fluid in question is thus indicative of these and other pathologic conditions.

The detection of high numbers of microparticles in blood and/or other bodily fluids would therefore be desirable, as it would be a reliable predictor of one or more of these pathological conditions. Additionally, presumably normal blood donors could be screened, by measuring the levels of microparticles in their blood, in order to determine whether they would be suitable platelet donors or for prophylactic purposes, i.e. to evaluate the patient's risk factors for diseases such as CVD. Particularly with respect to cardiovascular diseases (CVD), few effective tests or screening methods exist in order to permit the prediction of such diseases in patients or to determine the efficacy of a given treatment program. No rapid and easy-to-use test capable of accurately detecting high levels of all microparticles currently exists.

International patent application no. PCT/IB2005/000422, filed by Saga University on 21 Feb. 2005 and published as WO 2006/087597, describes a method of diagnosing cardiovascular disease by reacting an antibody to platelet-derived microparticles, and using the presence or absence of the platelet-derived microparticles in order to diagnose the cardiovascular disease. This system and method is however limited to the use of platelet antibodies and therefore is restricted to the detection and measurement of microparticles which are platelet-derived. These platelet-derived microparticles (PDMP) are those microparticles which are specifically released from platelets in association with platelet activation. Therefore, the method involves detecting an immune response against the PDMPs in a blood sample from the patient, for example by directly detecting the binding of platelet antibodies to the PDMPs. The PDMPs are, for example, detected by immunofluorescence as measured by flow cytometry.

However, a significant draw back exists with the above process described by Saga University. It is well known in the literature that patients with CVD primarily have microparticles in their blood which originate from endothelial cells. These endothelial cell originated microparticles are not platelet-derived, and therefore the above-described method is not capable of being used to detect abnormally high levels of these non-platelet derived microparticles.

As such, an improved method and system for the measurement of all microparticles in blood or other bodily fluid remains desirable, in order to better detect and diagnose a number of pathological conditions, including CVD.

In view of the shortcomings of the prior art, an improved method for detecting microparticles in a bodily fluid sample remains highly desirable.

SUMMARY OF THE INVENTION

The present method entails detecting the presence of a potentially deleterious or disease-related population of microparticles in a sample of bodily fluid, such as blood, urine, etc. The method serves both as a screening technique, in order to flag contaminated samples For further analysis, and as a diagnosis tool for detecting and evaluating many pathological conditions, such as cardiovascular disease, diabetes, kidney failure and the like. Using the present method, it is not necessary to know or determine the actual identity of the microparticles at the initial screening. Rather, the primary purpose of this technique is to identify that there is a significant quantity of the contaminant (i.e. the microparticles) in the bodily fluid tested.

Accordingly, in accordance with one aspect of the present invention, there is provided a method for diagnosing a pathological condition in a patient based on a bodily fluid from the patient, the method comprising steps of: using a dynamic light scattering (DLS) instrument to collect DLS measurements from the bodily fluid; using the DLS measurements to detect a presence of microparticles in the bodily fluid; and diagnosing the pathological condition based on the presence of said microparticles, the presence of the detected microparticles being indicative of the existence of the pathological condition in the patient.

There is also provided, in accordance with another aspect of the present invention, a method of screening for cardiovascular disease in a patient comprising: using a dynamic light scattering (DLS) instrument to collect DES measurements of a platelet rich plasma obtained from a blood sample from the patient; determining the presence or absence of microparticles in the platelet rich plasma using the DES measurements; and detecting cardiovascular disease in the patient based on the presence of the microparticles in the platelet rich plasma as determined by the DLS measurements.

There is further provided, in accordance with another aspect, a method of monitoring the efficacy of a treatment of a patient having a pathological condition, the method comprising: obtaining a sample of bodily fluid from the patient; using a dynamic light scattering instrument to collect dynamic light scattering measurements from the sample; determining a quantity of microparticles present in the sample based on the DLS measurements; determining a change in the quantity of the microparticles present relative to a predetermined base level of microparticles present in the bodily fluid prior to said treatment, and evaluating the efficacy of the treatment based on the determined change in the quantity of the microparticles present.

There is additionally provided, in accordance with yet another aspect, a method of monitoring the efficacy of a treatment for a patient having a pathological condition, the method comprising: obtaining a sample of bodily fluid from the patient; using a dynamic light scattering instrument to collect dynamic light scattering measurements from the sample; determining a quantity of microparticles present in the sample based on the DLS measurements; and evaluating the efficacy of the treatment based on a change in the quantity of the microparticles present in the sample.

There is further provided a method of predicting a risk for developing a pathological condition in a patient, the method comprising using dynamic light scattering (DLS) to detect a number of microparticles in a sample of bodily fluid from the patient, and determining a risk factor for the pathological condition based on the microparticles detected by DLS, the presence of said microparticles being associated with the existence of the pathological condition.

There is further provided a method of determining a risk factor of a patient developing a pathological condition, comprising: obtaining a sample of bodily fluid from the patient; using a dynamic light scattering instrument to collect dynamic light scattering measurements from the sample; determining a quantity of microparticles present in the sample based on the DLS measurements; and determining the risk factor predictive of the patient's risk of acquiring the pathological condition based on the detected quantity of microparticles in the sample, wherein the greater the quantity of microparticles present, the greater the patient's risk of developing the pathological condition.

BRIEF DESCRIPTION OF THE DRAWINGS

Further features and advantages of the present invention will become apparent from the following detailed description, taken in combination with the appended drawings, in which.

DETAILED DESCRIPTION OF EMBODIMENTS

Various embodiments and aspects of she present invention will now be described, including a method and system for diagnosing an existing medial condition or a possible medical condition by detecting microparticles in blood or other bodily fluids using dynamic light scattering (DLS), and a method of calibrating the device for quantitation of microparticles. A disposable container is also described within which whole blood can be separated into a red blood cell fraction and a plasma fraction, such that the level of microparticles within the plasma fraction can be measured in situ using DLS, thereby avoiding the need for pipetting the plasma fraction. A method and system for the characterization of microparticles detected by DLS is also described, involving the identification of optical characteristics either the detected microparticles or immunological markers such as fluorescently labeled antibodies or other light emitting chemicals which bind to certain microparticles.

The present application relates generally to the Dynamic Light Scattering method and system as described in Applicant's International Patent Application No PCT/CA2008/000212 filed Feb. 1, 2008, the entire contents of which is incorporated herein by reference. However, the present invention relates to the use of a dynamic light scattering system and method to detect microparticles and/or nanoparticles in blood and other bodily fluids, as an indicator of the presence of disease, an indicator of a risk of disease, and/or as a means of monitoring and evaluation efficacy of a treatment.

Figure 7A:
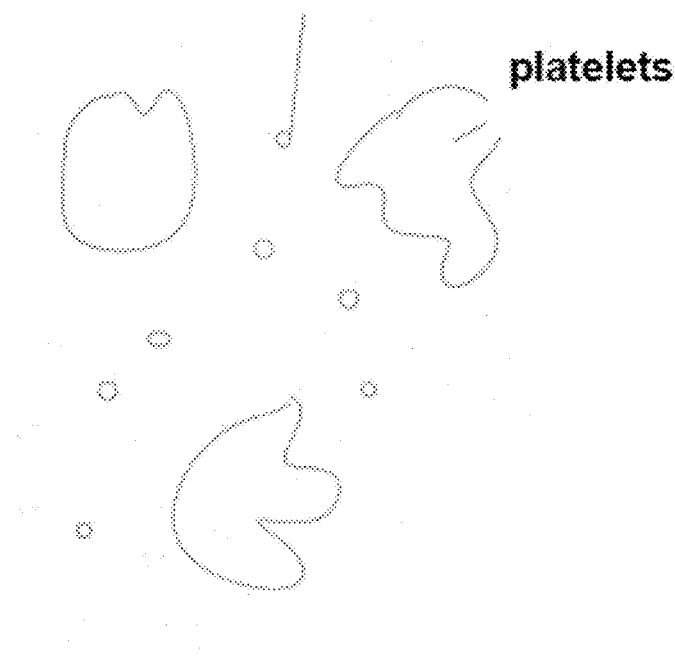
FIG. 7A is a schematic depiction of a blood sample having microparticles present therein.
Figure 7B:
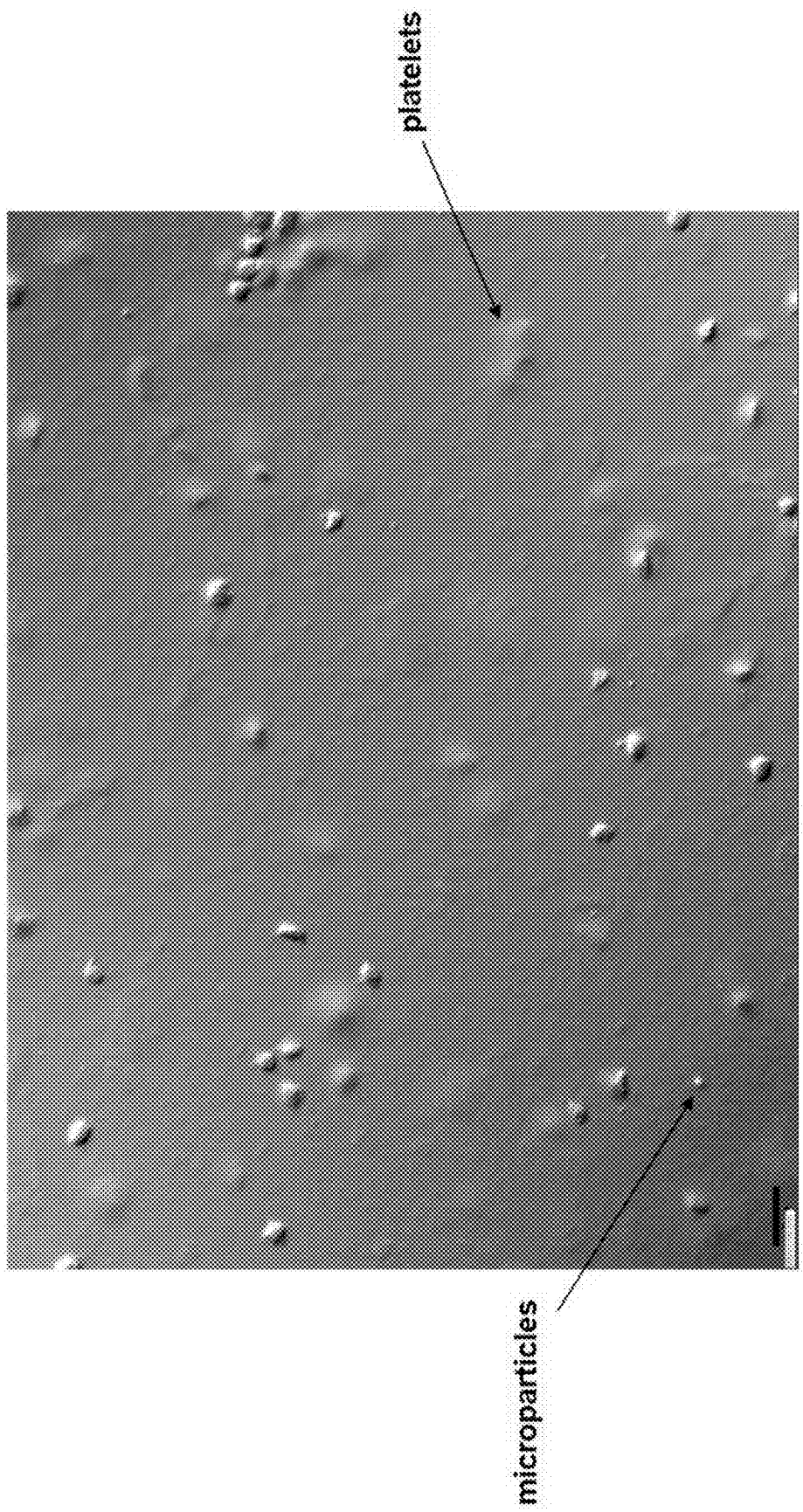
FIG. 7B is a differential interference contrast (DIC) microscopy image of a platelet rich plasma sample taken from a cardiovascular disease patient, showing the presence of microparticles in the fluid along with the bigger platelets.

The term "microparticles" as used herein is understood to mean particles within bodily fluids (such as blood), which have a hydrodynamic radius of less than about 1 micron, and may in one possible embodiment have a hydrodynamic radius of between approximately 20 and 1000 nm, and more preferably in another embodiment may have a hydrodynamic radius of between about 50 nm and 499 nm. The term microparticles as used herein is also intended to include so-called "nanoparticles". As seen in FIGS. 7A and 7B, microparticles are much smaller than the larger platelets in a platelet rich plasma blood sample for example. FIG. 7B shows an exemplary differential interference contrast (DIG) microscopy image of a platelet rich plasma sample taken from a cardiovascular disease patient, showing the presence of microparticles in the fluid along with the bigger platelets. The scale bar in the lower left corner of the image represents a size of 5 microns.

Although the present method of using DLS is primarily intended as a technique for detecting microparticles in a whole blood or platelet rich plasma sample as a means of diagnosis, it can be applied to measuring microparticle levels in other bodily fluids, such as whole blood, other blood products, urine, synovial fluid, cerebrospinal fluid, tears, as well as other biological fluids and colloids.

Figure 1A:
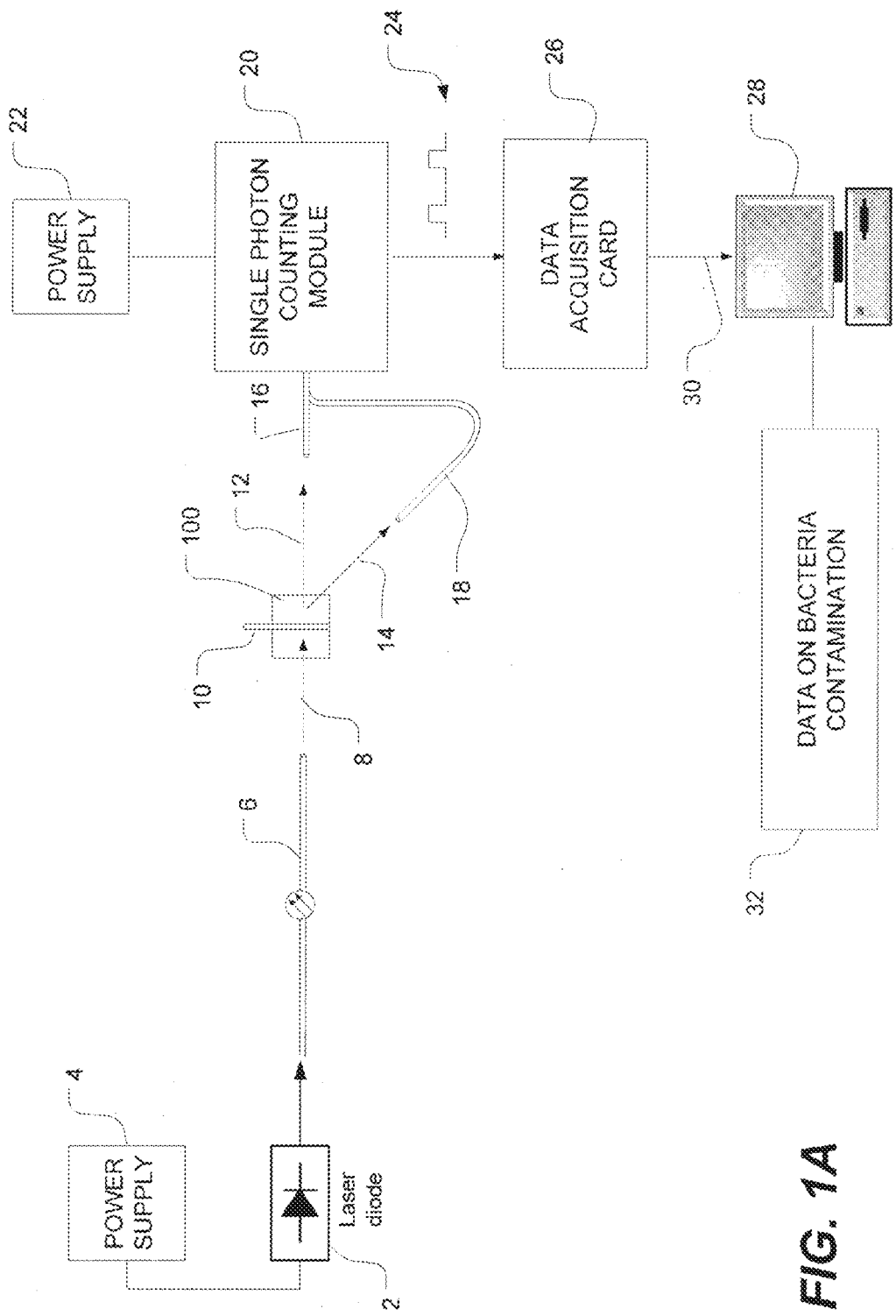
FIG. 1A is a schematic view of a DLS microparticle-detection system in accordance with a first embodiment of the present invention in which a capillary (or tube) containing a fluid sample is held substantially vertically for analysis.
Figure 1B:
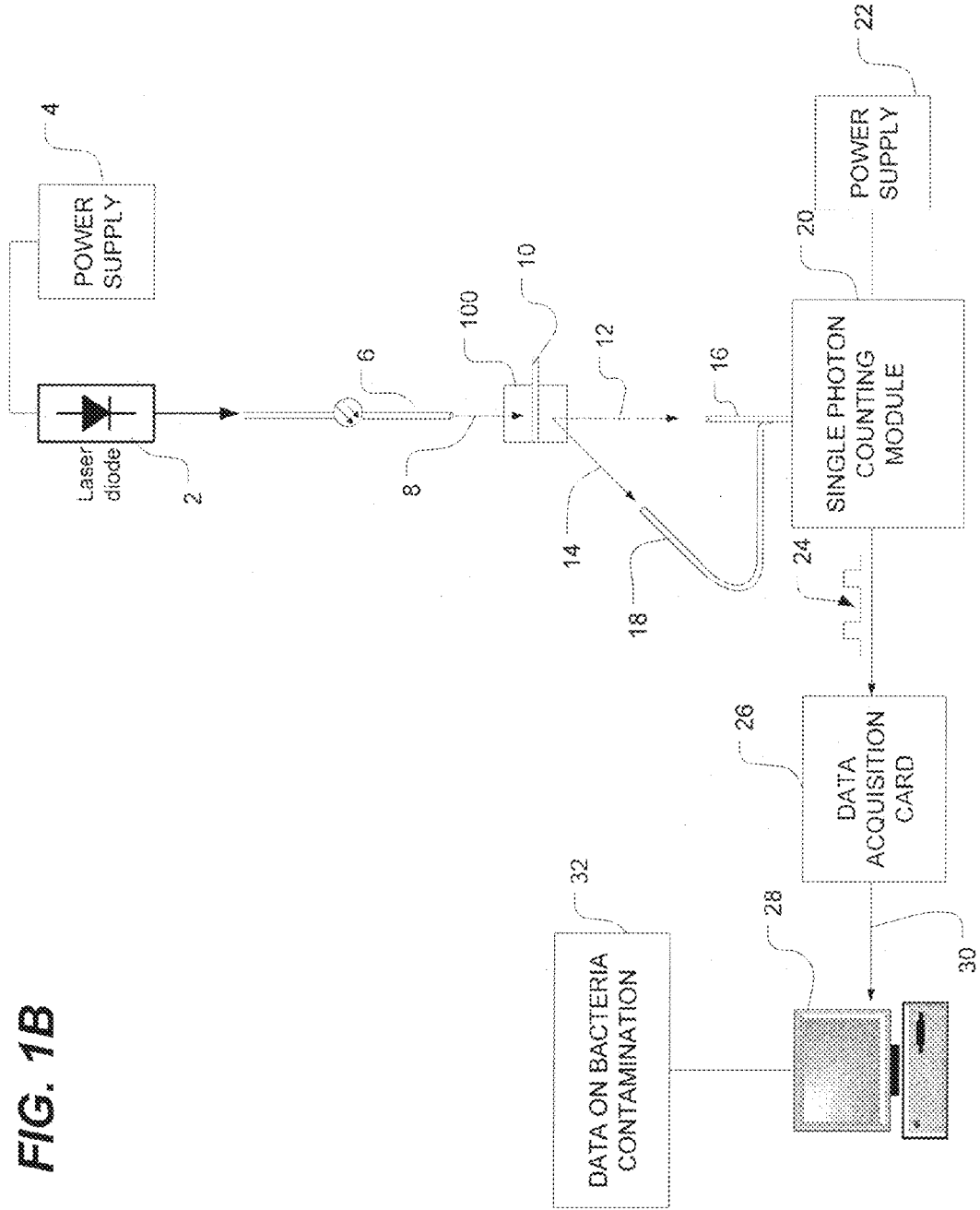
FIG. 1B is a schematic view of a DLS microparticle-detection system in accordance with a second embodiment of the present invention in which a capillary (or tube) containing a fluid sample is held substantially horizontally for analysis.

FIG. 1A is a schematic view of a microparticle detection system using dynamic light scattering (DLS), which is also known as quasi-elastic light scattering (QELS). As shown in FIG. 1A, the system has a light source such as, for example, a laser diode 2 which is powered by a power supply 4. The laser diode 2 generates and emits a beam of laser light into a length of optical fiber 6. The laser preferably generates light at 635 nm although other wavelengths could be used, as would be appreciated by those of ordinary skill in the art. As is also known in the art, the intensity of the laser beam can be adjusted using an adjustable neutral density filter (or by using an attenuator in the fiber) which allows the laser to be operated at maximum power while curtailing the intensity of the incident light. This reduces multiple scattering and other undesirable optical effects that arise when the intensity of the incident light is too high. The optical fiber is preferably a single-mode, polarization-maintaining optical fiber which, as is well known in the art, prevents the polarization from drifting when the light propagates through the optical fiber or, alternatively, a multimode fiber can be utilized. As is known in optics, polarization-maintaining fibers can be made using fibers of noncircular cross-section or by making the propagation medium of the fibers anisotropic such as, for example, by stressing the fibers in a specific direction. The polarized laser light emerges from the single-mode, polarization-maintaining optical fiber 6 and travels a short distance through the air (although it should be expressly understood that the distances shown in FIG. 1A are not meant to be representative or proportional to actual distances). This incident light impinges on the fluid sample (e.g. platelet plasma) contained within an at least partially transparent or translucent tube or container 10, as will be described in further detail below. The container 10 is held by a suitable sample holder 100, such as that described in International Patent Application No. PCT/CA2008/000212 filed Feb. 1, 2008. The sample holder 100 can be configured to retain the container 10 substantially vertically, as shown in FIG. 1A, or substantially horizontally, as shown in FIG. 1F. Although the container 10 is preferably a disposable capillary-type container as shown in FIGS. 1A and 1B, it may also include other configurations, such as a whole platelet, bag rather than a smaller capillary, in which case the sample holder 100 would receive or accommodate a whole platelet bag which includes an optical access window.

Referring back to FIG. 1A, the incident light scatters when photons strike the microparticles suspended in the fluid sample within the container 10. The scattered light 12, 14 scatters in various directions away from the fluid sample. A portion of this scattered light is collected by light collectors 16, 18, which are preferably optical fibers connected to a single-photon counting module 20 powered by a power supply 22. In one embodiment, the single-photon counting module 20 generates TTL pulses (transistor-transistor logic pulses) 24 and transmits these TTL pulses 24 to a data acquisition card 26. The data acquisition card 26 digitizes the TTL pulses and communicates the "raw data" to a software correlator running on a laptop or other computer 28. This raw data is communicated via a universal, serial bus (USB) 30 or other data bus or connector. Alternatively, the data acquisition and 26 can be installed within the computer 28. Together, the data acquisition card 26, computer 28 and software correlator constitute a "correlating means", as this expression is used in the present specification. Alternatively, the correlating means could utilize a hardware correlator (e.g. a multi-tau correlator) instead of the data acquisition card. The hardware correlator would generate and communicate a correlation function to the computer, although the data acquisition card and software correlator are preferred as it has been found to be more versatile and cost effective.

The size (i.e. hydrodynamic radius) of the microparticles within the fluid sample is obtained by correlating the observed speckle pattern that arises due to Brownian motion and solving the Stokes-Einstein equation, which relates the particle size to the measured diffusion constant, as is known in the art.

Figure 2:
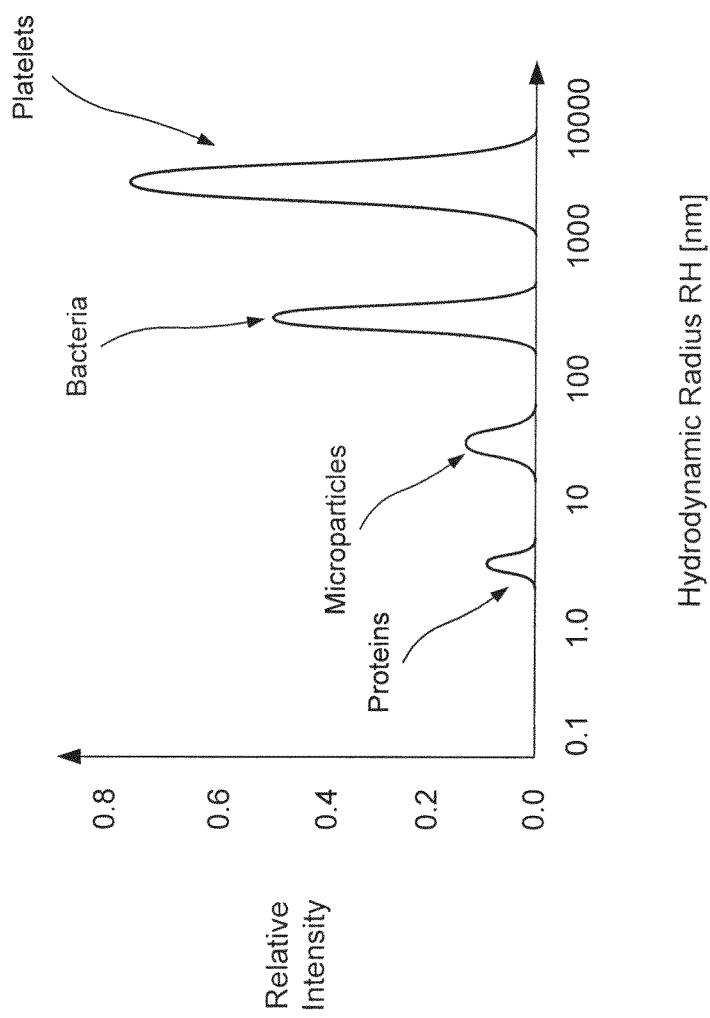
FIG. 2 is a graph plotting a representative distribution of hydrodynamic radii as a function of light intensity obtained from a DLS "speckle pattern" of platelets, bacteria, microparticles and proteins contained within a blood sample, as could be obtained using the DLS system shown in FIG. 1.

The computer 28 (running the software correlator) generates a correlation function and then generates a size distribution plot, such as the one shown in FIG. 2, for graphical presentation to a researcher, clinician, or other end-user. Alternatively, size distribution data can be presented in tabular form or in any other intelligible manner, such as for example by a summarizing single parameter. This single parameter can include, for example, the DLS score described in further detail below.

As depicted in FIG. 2, the size distribution plot shows a representative distribution of hydrodynamic radii for platelets, bacteria, microparticles and proteins detected within a fluid sample, as measured by the DLS system. The size of individual microparticles and/or the average size of all microparticles detected using the DLS measurements can be determined. However, it should be expressly understood that the hydrodynamic radii, relative intensities and particle distributions shown in FIG. 2 are but an example of a possible sample make-up. It is of note that such a distribution as measured in a fluid sample does reveal actual values and distributions of the particles present in the sample, however they are not comparable with those measured by more quantitative imaging, such as for example if one was to take a microscopy image and measure the real sizes of the particles. The hydrodynamic radii are calculated from the DLS "speckle pattern", as is known in the art. The size distribution plot readily enables researchers, technicians, clinicians or other end-users to detect the presence and level of microparticles in the fluid sample, for example of a whole blood or platelet rich plasma. This applies to both measurement types of dynamic scattering, i.e. not only forward scattering through a small capillary or similar device but also back scattering from a platelet bag with an optical access window or a flat (optically translucent) container.

The computer 28 generates and outputs (for example displays) the measured data 32, i.e. the level and make up of microparticles in the tested fluid sample. This data 32 generated by the computer 28 may include the quantitation of microparticles, as well as whether the quantity of microparticles exceeds a predetermined maximum threshold or fails below a predetermined minimum threshold. The computer can also attempt to identify the size and/or type of measured microparticles by comparing a measured hydrodynamic radius of the microparticles to previously obtained data and/or other empirical data. The computer 28 is also capable of providing an indication to the user, such as a visual or audible warning, which indicates that the measured quantity of microparticles falls outside the predetermined or expected normal envelope.

Accordingly, the DLS system is used to detect both the presence and level of microparticles within the fluid sample being tested, and the detected levels of microparticles can then be used to diagnose an existing disease or be used to evaluate the risk of contracting a disease for which the elevated levels of such microparticles is a precursor.

Contrary to other means which have been previously used to detect microparticles in blood, such as by reacting an antibody to platelet-derived microparticles and then using the presence or absence of the platelet-derived microparticles to diagnose a disease, the present DLS system is capable of detecting all types of microparticles within a number of bodily fluids, and is therefore not limited only to the detection of platelet-derived microparticles as is the existing prior art. The present DLS system is therefore much more versatile, rapid and easy-to-use than the method of detecting platelet-derived microparticles by immunofluorescence, as measured by flow cytometry, employed in the prior art.

Another possible use of the present DLS system to detect the presence and/or quantity of microparticles in a blood or other bodily fluid sample is as a method to monitor ongoing treatment of a patient. For example, hemodialysis can be monitored by measuring the number of microparticles in the blood, or the measured level microparticles in a platelet rich plasma sample can be used to predict the patient's risk of developing cardiovascular disease or the efficacy of an ongoing treatment.

As noted above, a container 10 within which the fluid sample to be tested by DLS is used which allows the direct DLS measurement of the fluid contained therein. The container is preferably a disposable capillary having at least one enclosed end. In experimental tests, a glass capillary that was melted to close the bottom end was used. It is to be understood, of course, that suitable disposable capillary containers can be made. In accordance with one aspect of the present invention, this disposable container 10 is a separator capillary which is used in order to separate whole blood into a red blood cell fraction and a platelet rich plasma (PRP) or platelet poor plasma (PPP) fraction, i.e. within the capillary itself. This may be done, for example, by centrifuging the separator capillary and then using this same capillary container within the sample holder 100 such that the laser light of the system can be directed through the platelet rich plasma layer directly within the capillary container. Preferably, the sample container 10 is a disposable, glass or plastic capillary having at least one enclosed end (in order to permit centrifuge of the container 10). The capillary may have a round or square geometry, a diameter of about 2 mm and a volume of about 30 microliters, although the sample holder 100 is designed to accommodate a range of sizes and therefore these dimensions should not be considered as limiting the scope of the invention.

In order to demonstrate the effectiveness of the use of DLS to detect and measure the quantity microparticles in a fluid sample, the following tests were conducted.

Figure 3:
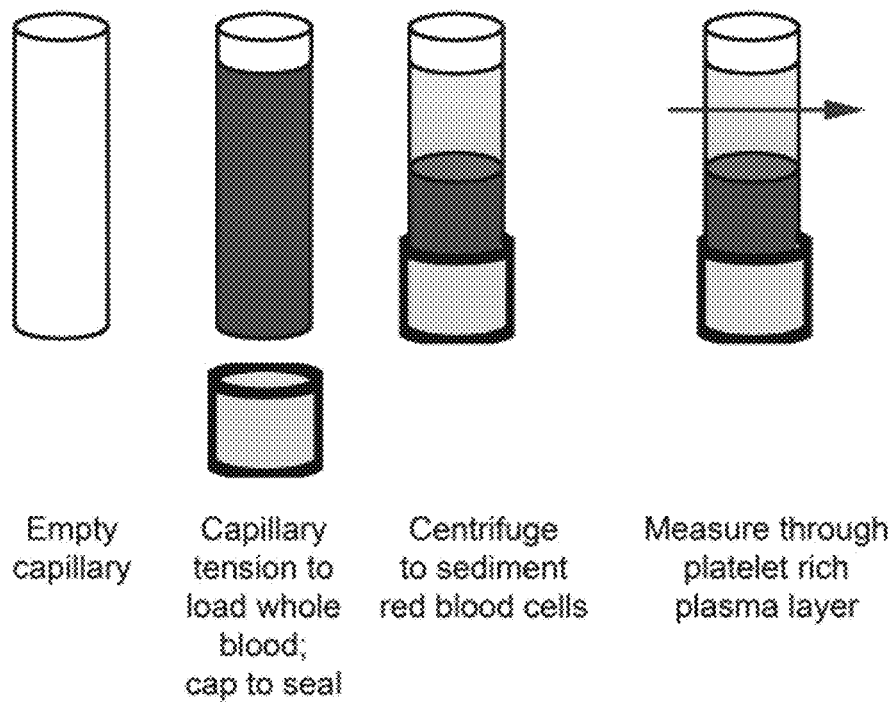
FIG. 3 is a schematic perspective view of a capillary which is filled with a whole blood sample and centrifuged to sediment the red blood cells, in order to allow dynamic light scattering measurement through the platelet rich plasma above the red blood cell and the white blood cell layers.

First, as shown in FIG. 3, empty glass capillaries (i.e. the containers 10) having a closed bottom end were tensioned to load approximately 45 μL of whole blood therein and capped to seal the capillaries. The sample was allowed to settle (accelerated by centrifugation) such that the red blood cells were allowed to sediment to the bottom, leaving a platelet rich plasma layer on top within the capillary.

The capillaries were then placed in a sample holder 100 of a DLS system as described above, and the DLS system was used, as described herein, to measure the quantity of microparticles (and nanoparticles) in the platelet rich plasma fraction within the capillary container.

Figure 4:
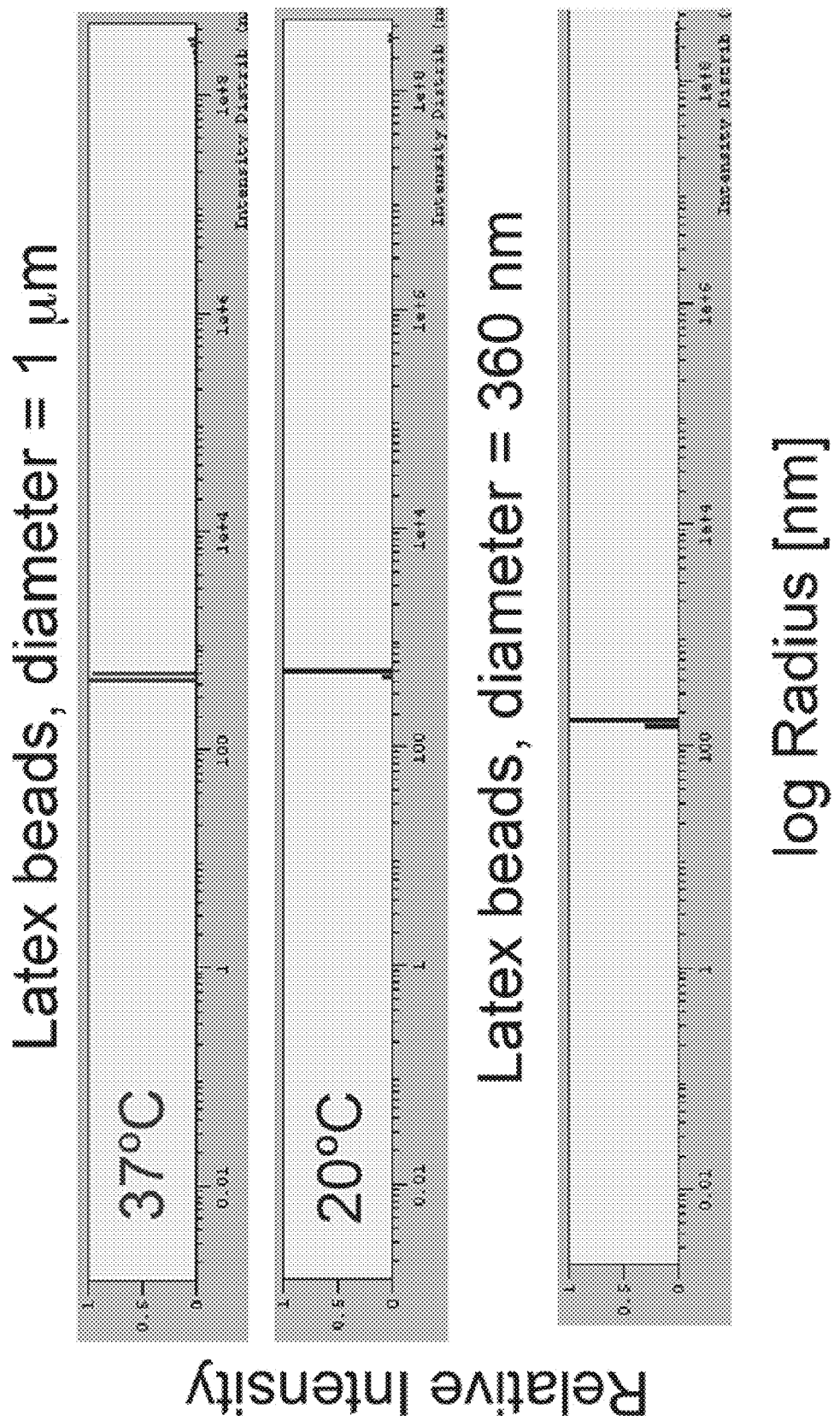
FIG. 4 is DLS-derived particle size distribution graph, depicting the presence of detected calibration heads in the size range of microparticles in a fluid sample.
Figure 5:
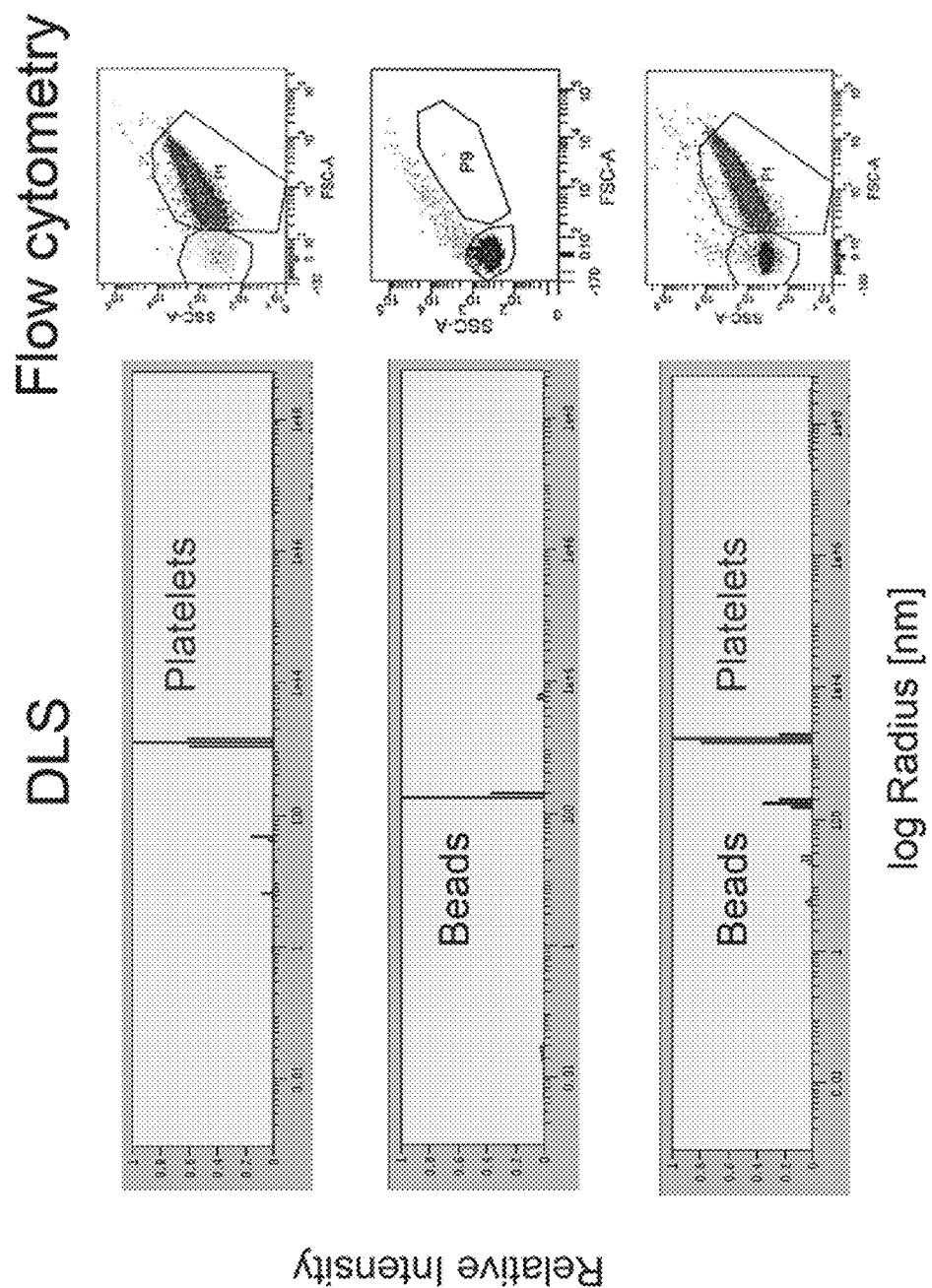
FIG. 5 is a DLS-derived particle size distribution graph of a blood sample, depicting the platelet and bead sizes and their relative intensities.

In order to calibrate the DLS device for accurate quantitation of the microparticles within both such platelet rich plasma and other biological fluids, calibration beads of a known number and size were added to test samples of such fluids, and the DLS system was used to quantitate the microparticles present, relative to the calibration beads. The calibration beads were of a size corresponding to an expected size of microparticles known to exist when a pathological dondition is present. This calibration process is shown in FIGS. 4 and 5 for example, in which DLS results show the peak in relative intensity of the light scatter corresponding to latex calibration beads of a known size (ex: 1 μm) for tests conducted at two different temperatures (20° C. and 37° C.). As can be seen in FIG. 5, the DLS system is able to identify the calibration beads relative to the platelets in the sample, which have different sizes (hydrodynamic radii). Once so calibrated, the DLS system can be accurately and reliably used to detect the quantity and sizes of the microparticles present in the biological fluid to be tested.

Figure 6:
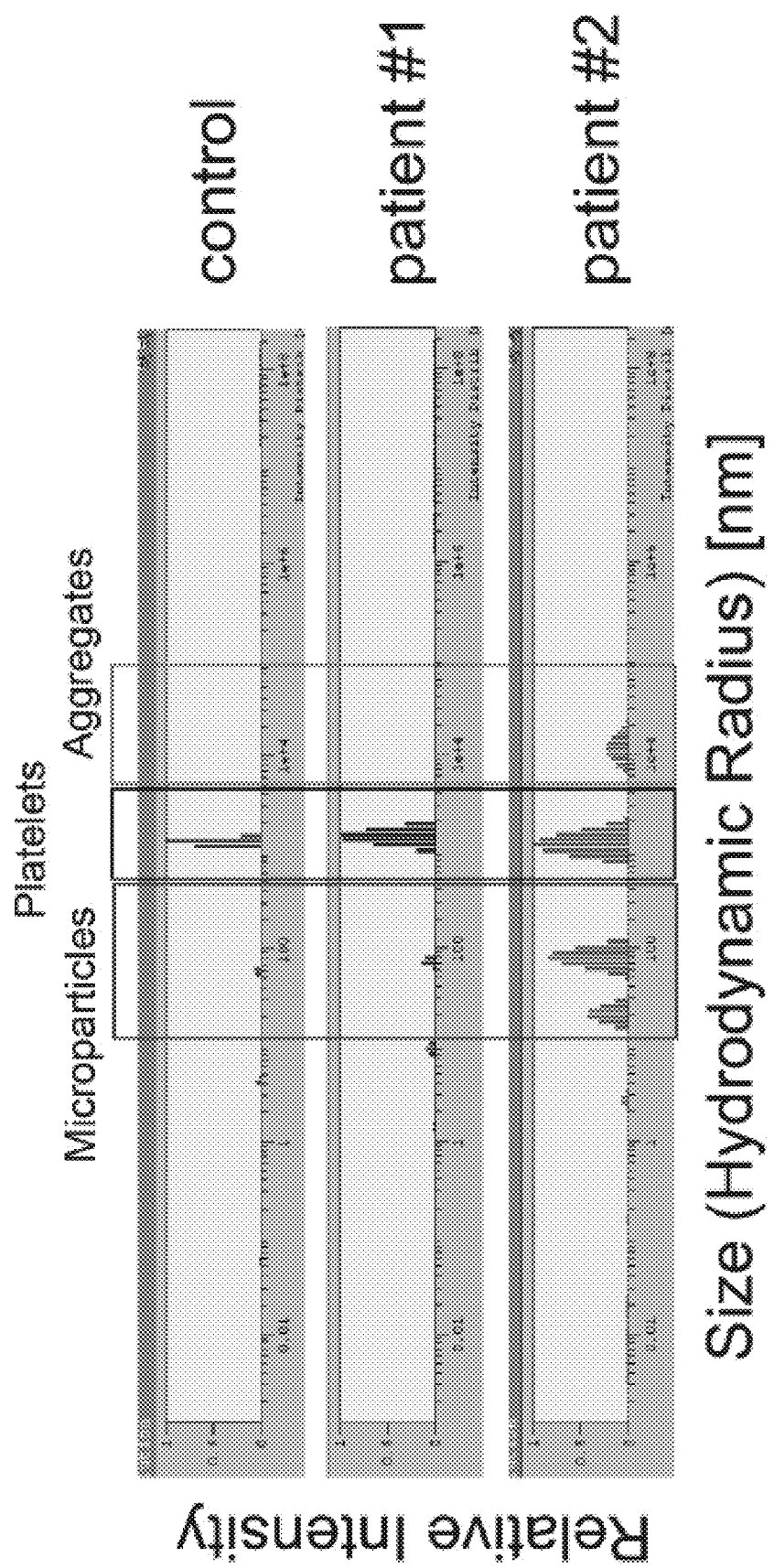
FIG. 6 is a DLS-derived particle size distribution graph of samples from an experiment conducted on a control patient and a test group of patients, showing patient #1 having a number of microparticles corresponding to the control group and an abnormal level of microparticles in patient #2.

Referring now to FIG. 6, the results of test conducted on fresh whole blood samples from nine cardiology patients, after the placement of stents in their coronary arteries and a loading dose of 600 mg of clopidogrel, are shown. The patients were treated with a daily dose of 75 mg clopidogrel for up to 12 months. As seen in FIG. 6, results from the DLS system analysis of the platelet rich plasma (PRP) from a control donor (i.e. one having no microparticles in their blood sample) relative to that of the nine cardiology patients tested is shown. As can be readily seen, the tested PRP of "patient #1", which was representative for 8 of the 9 actual patients, had little or no microparticles detected by the DLS system, indicating a positive response to the treatment 12 months after the placement of the stent and therefore little or no risk for imminent recurrence of a cardiovascular problem. However, she tested PRP sample of 'patient #2', which was representative of 1 of the 9 actual patients, revealed a significant number of microparticles in the PRP 12 months after the placement of the stent, and therefore indicates little treatment response in this patient and thus high risk for adverse future events such as re-stenosis or myocardial infarction. The DLS measurement and analysis therefore found patient #2 to be at continued risk for CVD following the procedure, and accordingly the results of the DLS detection of high levels of microparticles in this patient's blood were found to be strongly indicative of the continued presence of CVD in the patient. The present method can therefore be used for the continued monitoring of patients post-intervention, in order to determine the success of the invention and therefore whether or not the disease remains.

Additionally, further testing and analysis of frozen PRP from 13 other patients was also conducted at five different times, namely: 1) before the same percutaneous intervention (PCI), i.e. to place a stent in the coronary artery; 2) 24 hours following the PCI; 3) 1 month following the PCI; 4) 6 months following the PCI; and 5) 12 months following the PCI. All samples analyzed revealed a high level of microparticles, i.e. showing a distribution similar to that of patient #2 in FIG. 6, with the highest concentration of microparticles 24 hours after the PCI.

Although principally the present method is intended to comprise the detection of microparticles using DLS, the DLS system can also be used to simultaneously determine additional characteristics of the blood or other bodily fluid sample, such as platelet quality for example. The determination of platelet quality is done based on three independent factors, namely (i) the mean hydrodynamic radius of the platelets, (ii) the relative number of microparticles (MPs) and (iii) the platelet response to temperature cycling. A computational matrix quantifies platelet quality as a function of mean hydrodynamic radius (RH), MP concentration, and temperature response (TR). The three measures are combined to one number called the "DLS score", which enables automated platelet scoring because the system can simultaneously measure and input into the computational matrix all three of these independent parameters, thus providing very high analytic sensitivity for platelet quality determinations. This methodology is described in detail in Applicant's U.S. Pat. No. 7,341,873 issued Mar. 11, 2008 and entitled METHOD FOR DETERMINATION OF PLATELETS QUALITY, the content of which is incorporated herein by reference. It should be expressly understood that this system can be used not only for DLS analysis of platelets in suspension, but also for analyzing whole blood or other colloids or colloidal dispersions. Therefore, the relative number of microparticles in the fluid sample being measured can be used both as described above, i.e. as indicative of the presence or the risk of disease, as well as to part of the determination platelet quality.

The present systems therefore can detect microparticles within the blood or other fluid sample using DLS, and therefore provide indication of a disease or risk of a disease which may be associated with the measured level microparticles. As the number of microparticles is also used to determine platelet quality as noted above (i.e. whether the platelets are "fresh", that is of good quality, or "stale", that is no longer useful for transfusion), based on the calculated DLS score, these two determinations can either be made in parallel or individually. Both of these tests/assessments can provide crucial information about the PRP from whole blood prior to a transfusion, thus minimizing the risks that poor quality platelets, pathologic agents and/or disease present in the sample. Furthermore, because the system is easy to use, highly sensitive and provides quick results, it becomes a natural candidate as a point-of-care (pre-transfusion) test, in order to identify a number of possible pathological conditions, such as cardiovascular disease, diabetes, renal failure, etc. Further, by measuring the level of microparticles in a patient's blood over time, the efficacy of a treatment conducted to help cure and/or alleviate the disease can be determined based on the measured levels of microparticles detected.

The present method for detecting microparticles in a fluid sample, such as a platelet rich plasma (PRP) from whole blood for example, therefore includes steps of placing the sample in a dynamic light scattering (DLS) instrument, collecting DES measurements from the sample, and detecting microparticles in the sample based on the DES measurements from the sample. The method may further include determining an exact quantity of microparticles present, and then comparing the determined quantity of microparticles to existing data relating number of particles to predetermined pathological conditions.

In one embodiment, the step of detecting microparticles in the sample involves steps of determining a relative intensity of scattered light relative to incident light for a range of particle sizes to thus create a size distribution having discrete peaks corresponding to different types of particles. All components contained in the blood sample, such as platelets, microparticles, proteins and bacteria, are then discriminated based on expected locations of the discrete peaks in the size distribution. The quantity of microparticles in the sample can then be determined based on the relative intensity of the scattered light found at a particle size, or size range, that is known to correspond to the particle size(s) of the microparticles.

For example, as seen in FIG. 2, the quantity of microparticles in the measured sample can be determined based on the relative measured intensity of the scattered light at the peak corresponding to the known hydrodynamic radius (RH) of the microparticles (i.e. between 10 and 100 nm) in the hypothetical example shown.

In one embodiment, the step of detecting microparticles present in the sample may also entail characterizing the microparticles detected, such as by identifying a specific origin, type and/or size (i.e. hydrodynamic radius) of microparticles in the sample by correlating a measured mean size of the microparticles to previously determined empirical data. This can include, for example, correlating determined microparticle numbers and/or sizes to those present in existing data, in order to diagnose a specific disease condition known to correspond to the measured set of microparticle characteristics. In other words, mean microparticle size may be obtained using the DLS instrument for various microparticles, thereby allowing for the prediction of the disease which may be associated with the types and numbers of such microparticles.

Therefore, in addition to simply identifying the presence of microparticles, or abnormally high levels thereof, which is believed to be sufficient in most cases in order to diagnose the existence of a pathological condition, the DLS system can also be used to characterize the microparticles detected by the dynamic light scattering. This is accomplished by an additional, fiber optic system that is built into the DLS instrument, and which uses an additional low-cost laser and an optical fiber to illuminate the microparticles and the calibration beads described above contained within the fluid sample. The specific optical characteristics the detected microparticles immunologic markers, such as fluorescently labeled antibodies or other light emitting chemicals that bind to certain microparticles, can thereby be determined. Thus, pre-established test kits can be provided for specific sample treatment in order to characterize the types of microparticles present.

However, it should be borne in mind that, using the present method, it is not necessary to know or determine the actual identity of the microparticles upon an initial screening of the fluid sample, in order to be an effective diagnostic tool. Rather, the primary purpose of this technique is to identify that there is a significant quantity of the contaminant (i.e. the microparticles) in the bodily fluid tested. This significant quantity of microparticles is sufficient to permit the diagnosis of disease or to predict the likelihood of one developing. The present method can thus be used both as a diagnosis and/or screening method, in order to flag contaminated samples for further analysis and as a diagnosis tool for detecting and evaluating pathological conditions, as well as being able to more specifically characterize the microparticles present. For example, by using the DLS instrument to measure at different scattering angles, one can discriminate what scattered light is collected in order to look at and consider specifically certain microparticle populations. The existence of disease can therefore be diagnosed based on the DLS determined levels of microparticles, as indicated by the total scattering intensity. After calibration of the DLS device with known concentrations of standard latex beads, as described above, a significantly higher total scattering intensity indicates a high number of microparticles.

The foregoing thus provides a method of detecting abnormal levels of microparticles using dynamic light scattering, which has been found to be a strong predictor of the presence of pathological conditions. The microparticles detected by DLS can further be characterized, for example by their size distribution determined from the DLS signal.

The presence of microparticles in the fluid sample causes a distinctive DLS signal (e.g. a recognizable peak in an expected range of particle size corresponding to microparticles) that is distinct from other particles in a PRP from whole blood (such as platelets, bacteria, and proteins). As DLS is able to detect the presence of all types of microparticles, and not just those which might be platelet-derived, it is believed that this technique is a easy-to-use and universally applicable method of diagnosing a potential medical condition based on the detection of abnormally high levels of microparticles in the blood or bodily fluid being tested by DLS.

DLS scoring, as described herein, using the DLS system can be calculated as follows:

$$DLS\ score = \left[\sum_{temp1}^{tempN} ((R_1 - SD_1) * I_1 - (R_2 - SD_2) * I_s)\right] \div 100$$

Where:
$R_1$=mean radius of particles with radius 500 nm-2500 nm (i.e. the "Platelet Size")
$SD_1$—standard deviation of the $R_1$ particle distribution (the narrower the distribution the better)
$I_1$=normalized intensity of the $R_1$ particle distribution (contribution of all particles totals 1)
$R_2$=particles 50 nm-499 nm in radius . . . microparticles
$SD_2$=standard deviation of she $R_2$ particle distribution (the narrower the distribution the better)
$I_2$=normalized intensity of the $R_2$ particle distribution (contribution of all particles totals 1) which is known herein as the "Relative Number of Microparticles"

Σ=sum over all temperatures 1 to N (e.g., 37_1, 20, 37_2) divided by 100, which is known herein as the "Temperature Response"

In a variant, an abbreviated score can be calculated by utilizing the DES system to measure the fluid in a sample bag, wherein DLS measurements are obtained through an optical access window in the wall of the bag. For example, this sample bag could be a small flattened out part of the tubing of an IV line or alternately a much larger dialysis bag, for example. DLS scoring with this arrangement is performed at room temperature, whereas the DLS scoring using the arrangements of FIGS. 1A and 1B allow for temperature variation during the DLS tests. While it is abbreviated, it is also less accurate.

From the foregoing explanation on DLS scoring, it should be apparent that this formula combines all DLS parameters into one number or "score" and parallels the scoring scheme based on clinical outcome. In the foregoing, "transfusion merit" is defined as the sum of the 1 h corrected count increment (CCI) and the 24 h CCI: transfusion merit score=1 h CCI+24 h CCI. In clinical practice, an acceptable 1 h CCI is 7 or higher and an acceptable 24 h CCI is 5 or higher. Thus, the minimum acceptable transfusion merit is 12.

The "sample quality" (i.e. quality of a given PRP from whole blood) can thus be determined with reference to this DLS score. If the DES score is less than 12, the unit would be discarded as being contaminated. If the DLS score is 12 or higher, then the concentrate is still considered useable or viable for transfusion or other uses. Persons of ordinary skill in the art will appreciate that this threshold score of 12 is an arbitrary cutoff (based on Applicant's correlation of the DLS score with other bacteria measurements and/or acceptable levels) and may be changed.

DLS measurements of a bodily fluid sample using the present DLS system will show spikes at certain particle sizes, one of which is indicative of microparticles within the fluid. Therefore, a method of using dynamic light scattering (DES) for diagnosing a potential medical condition by detecting microparticles in a sample of a bodily fluid is provided, and is accomplished in one possible embodiment by (a) obtaining DES measurements on the sample by illuminating the sample with incident light and by collecting the scattered light; (b) determining a particle size distribution based on the scattered light; (c) identifying a cluster of particles on the particle size distribution that is representative of microparticles of an expected size range; and (d) diagnosing the disease by the presence of the microparticles.

The DLS measurements can yield a particle size distribution, such as the one shown in FIG. 2. On the distribution, there may be one or more peaks (or "clusters") representing discrete and distinct populations of particles. One of those peaks represents the population of microparticles. The presence or absence of further peaks or clusters representing other populations of particles (platelets, bacteria, contaminants, etc.) can be used to determine whether there exists a pathological condition of which the measured level of microparticles is representative.

The relative number of microparticles in a sample can also be determined by calculating the DES score, which includes the number of microparticles detected in the fluid. Therefore, the risk of a pathological condition can be predicted by identifying an unduly high quantity of microparticles in the fluid sample, which is determined by: (a) obtaining DES measurements from the fluid sample; (b) determining whether a DLS score that is computed based on the DLS measurements is outside a predetermined range; and (c) flagging the fluid sample as being an indicator of risk of the pathological condition when the DLS score is outside the predetermined range.

In one embodiment, the DES score can be computed as $$\text{DLS score}=[(R_1-SD_1)*I_1-(R_2-SD_2)*I_2]*0.03$$

Where:
$R_1$=mean radius of particles with radius 500 nm-2500 nm (i.e. the "Platelet Size")
$SD_1$=standard deviation of the $R_1$ particle distribution (the narrower the distribution the better)
$I_1$=normalized intensity of the $R_1$ particle distribution (contribution of all particles totals 1)
$R_2$=particles 50 nm-499 nm in radius ("microparticles")
$SD_2$=standard deviation of the $R_2$ particle distribution. (the narrower the distribution the better)
$I_2$=normalized intensity of the $R_2$ particle distribution (contribution of all particles totals 1) which is known herein as the "Relative Number of Microparticles".

The embodiments of the invention described above are intended to be exemplary only.

The invention claimed is:

1. A method of assessing a sample of bodily fluid containing platelets, comprising the steps of:
using a dynamic light scattering (DLS) instrument to collect DLS measurements from the sample;
using the collected DLS measurements to detect a presence of microparticles in the sample and to determine a number of said microparticles of a particular size range relative to a determined number of larger reference particles also detected in the sample, wherein the microparticles of said particular size range are bacteria.

2. The method according to claim 1 wherein the larger reference particles are platelets.

3. The method according to claim 2 wherein the microparticles detected of said particular size range have a hydrodynamic radius of between about 10 nm and 500 nm.

4. The method according to claim 1 including the step of calculating a DLS score based on the detected presence of microparticles in the sample and the number of microparticles of a particular size range relative to the number of larger reference particles, the DLS score being indicative of a transfusion merit of the sample.

5. The method according to claim 4 including the step of making a determination that the sample is contaminated and not transfusable if the DLS score is less than 12.

6. The method according to claim 4 including the step of making a determination that the sample is viable for transfusion if the DLS score is greater than 12.

7. The method according to claim 1, further comprising the step of comparing the relative number of microparticles to a predetermined minimum level of microparticles known to exist when a pathological condition is present.

8. The method according to claim 1 in which the sample is obtained by separating a blood sample into a red blood cell fraction and platelet rich plasma (PRP) within a fluid container, and disposing the fluid container in the DLS instrument to collect DLS measurements on the PRP in the fluid container.

9. The method according to claim 8 further comprising loading the blood sample into the fluid container before the step of separating, the fluid container being a disposable capillary.

10. The method according to claim 1 further comprising using the DLS measurements to determine at least one of a quantity and average size of the microparticles detected in platelet rich plasma (PRP).

11. The method according to claim 1 further comprising the step of characterizing the microparticles detected in the sample by the DLS by identifying a specific origin, type and/or size of microparticles.

12. A method of assessing a sample of bodily fluid containing platelets, comprising the steps of:
   using a dynamic light scattering (DLS) instrument to collect DLS measurements from the bodily fluid;
   using the DLS measurements to detect a presence of microparticles in the bodily fluid and to determine a number of said microparticles of a particular size range relative to a determined number of larger reference particles also detected in the bodily fluid; and
   diagnosing a pathological condition based on the determined number of said microparticles relative to said larger reference particles, the presence of the detected microparticles of said particular size range being indicative of the existence of a pathological condition in a patient from whom the sample was collected.

13. The method according to claim 12 wherein the larger reference particles are platelets and the microparticles detected of said particular size range are bacteria.

14. A method of assessing a sample of bodily fluid containing platelets, comprising the steps of:
   using a dynamic light scattering (DLS) instrument to collect DLS measurements from the sample;
   using the collected DLS measurements to detect a presence of microparticles in the sample and to determine a number of said microparticles of a first size range relative to a determined number of reference particles of a second, larger size range also detected in the sample, the microparticles of the first size range comprising bacteria;
   establishing a particle size distribution from the DLS measurements, the particle size distribution comprising at least a first population corresponding to the microparticles of the first size range and a distinct second population corresponding to the larger reference particles; and
   determining the quantity of microparticles of the first size range in the sample by comparing the first population to the second population.

15. The method according to claim 14 wherein the larger reference particles are platelets.

16. The method according to claim 14 further comprising the step of comparing the number of microparticles of the first size range to a predetermined level of microparticles known to exist when a pathological condition is present.

17. The method according to claim 14 including the step of calculating a DLS score that correlates to the quality of the sample.

* * * * *